United States Patent [19]

Tseng et al.

[11] 4,338,213

[45] Jul. 6, 1982

[54] AQUEOUS CHEMILUMINESCENT SYSTEMS

[75] Inventors: Shin-Shyong Tseng; Michael M. Rauhut, both of Bridgewater, N.J.

[73] Assignee: American Cyanamid Company, Stamford, Conn.

[21] Appl. No.: 253,327

[22] Filed: Apr. 13, 1981

Related U.S. Application Data

[60] Division of Ser. No. 122,621, Feb. 19, 1980, Pat. No. 4,282,357, which is a continuation-in-part of Ser. No. 956,567, Nov. 1, 1978, Pat. No. 4,226,738.

[51] Int. Cl.$^3$ .............................................. C09K 3/00
[52] U.S. Cl. ......................................... 252/188.3 CL
[58] Field of Search ................................ 252/188.3 CL

[56] References Cited

U.S. PATENT DOCUMENTS

3,354,156 11/1967 Wendt et al. ........................ 544/85
4,006,140 2/1977 Son ....................................... 544/85

*Primary Examiner*—Richard Raymond
*Attorney, Agent, or Firm*—Gordon L. Hart

[57] ABSTRACT

Quaternary salts of N,N'-bis(morpholinoalkyl)-N,N'-bis(trifluoromethylsulfonyl)oxamides and of N,N'-bis(pyridylalkyl)-N,N'-bis(trifluoromethylsulfonyl)oxamides are useful for generation of chemiluminescence by reaction with hydrogen peroxide in aqueous solvent.

14 Claims, No Drawings

AQUEOUS CHEMILUMINESCENT SYSTEMS

The invention, described herein, was made in the performance of work supported by the Office of Naval Research (Contract No. N-00014-77-C-0634), and is subject to the provisions of ASPR 7-104.18, December, 1969, and ASPR 7-302.23(b) long form August, 1977. This is a division of application Ser. No. 122,621, filed Feb. 19, 1980, now U.S. Pat. No. 4,282,357, which is a continuation-in-part of application Ser. No. 956,567 filed Nov. 1, 1978, now U.S. Pat. No. 4,226,738.

This invention relates to novel compounds and compositions containing them which are useful for the generation of chemiluminescent emission, that is, the generation of electromagnetic radiation at Wavelengths between 330 and 1,000 nanometers by means of a chemical reaction.

The art of generating light via chemical energy, that is, chemiluminescence, by the reaction of an oxalic acid ester with a hydroperoxide in the presence of a fluorescer compound in aqueous systems, has been disclosed in U.S. Pat. No. 4,053,430. However, there is a need for aqueous chemiluminescent compositions, as emergency sources of light, which have higher light intensities and efficiencies than those disclosed in this patent.

In accordance with the present invention, there is provided a novel class of water-soluble amides of oxalic acid represented by the formula (I):

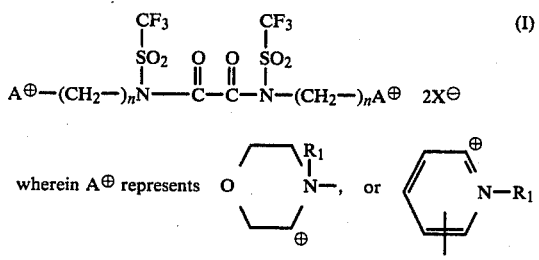

wherein $R_1$ is hydrogen, or alkyl $(C_1-C_6)$, n is an integer from 2 to 6, and $X^\ominus$ is an anion. When a diamide of this formula is mixed with an aqueous solution of a water-soluble organic fluorescer having a spectral emission in the range of 330 to 1,000 nanometers, with hydrogen peroxide, or a source of hydrogen peroxide, the mixture produces a chemiluminescent emission of high intensity and efficiency.

Typical oxamides of formula (I), which may be employed, are those compounds wherein the anion is selected from chloride, bromide, fluoride, methanesulfonate, methosulfate, trifluoromethanesulfonate, tetrafluoroborate, and the like.

Aqueous systems containing the water-soluble oxamides of formula (I) are more efficient than the aqueous systems containing water-soluble esters of oxalic acid described in the prior art.

The preferred compounds of formula (I) are those having an anion which is not oxidized by hydrogen peroxide in the chemiluminescent compositions.

The term "hydrogen peroxide compound," as used herein, means hydrogen peroxide or a compound that produces hydrogen peroxide by reaction or decomposition.

The novel oxamides of this invention may be obtained by reacting two moles of a sulfonamide with one mole of oxalyl chloride in an anhydrous organic solvent, such as tetrahydrofuran, under an inert atmosphere. The oxamide may be converted to the corresponding trifluoromethanesulfonate, methanesulfonate, p-toluene sulfonate, methosulfate, chloride, bromide, or fluoride, by quaternization reactions which are well-known.

Illustrative examples of compounds of formula (I) within the purview of this invention include the dihydrochlorides, dihydrobromides, dihydrofluorides, di(-trifluoromethane)-sulfonates, dimethanesulfonates, dimethosulfates, and ditetrafluoroborates of the following compounds:

N,N'-bis(2-morpholinoethyl)-N,N'-bis(trifluoromethylsulfonyl)oxamide,
N,N'-bis(3-morpholinopropyl)-N,N'-bis(trifluoromethylsulfonyl)oxamide,
N,N'-bis[2-(2-pyridyl)ethyl]-N,N'-bis(trifluoromethylsulfonyl)oxamide,
N,N'-bis[3-(2-pyridyl)propyl]-N,N'-bis(trifluoromethylsulfonyl)oxamide,
N,N'-bis(6-morpholinohexyl)-N,N'-bis(trifluoromethylsulfonyl)oxamide,
N,N'-bis[2-(4-pyridyl)ethyl]-N,N'-bis(trifluoromethylsulfonyl)oxamide,
N,N'-bis[5-(3-pyridyl)pentyl]-N,N'-bis(trifluoromethylsulfonyl)oxamide, and the like.

Illustrative examples of sulfonamides, which may be reacted with oxalyl chloride to prepare the above oxamides, include:

N-(2-morpholinoethyl)trifluoromethanesulfonamide,
N-(3-morpholinopropyl)trifluoromethanesulfonamide,
N-[2-(2-pyridyl)ethyl]trifluoromethanesulfonamide,
N-[3-(2-pyridyl)propyl]trifluoromethanesulfonamide,
N-[2-(4-pyridyl)ethyl]trifluoromethanesulfonamide,
N-[5-(3-pyridyl)pentyl]trifluoromethanesulfonamide,
and the like.

The fluorescer compounds, useful in the chemiluminescent compositions of this invention, may be defined broadly as water-soluble compounds, having an emission spectral maximum between 330 and 1,000 nanometers, which do not react with a hydrogen peroxide compound or the amide of oxalic acid on contact.

Numerous fluorescer compounds having the abovedescribed properties are known. Many of these compounds are described in "Fluorescence and Phosphorescence" by Peter Pringsheim, Interscience Publishers, Inc., New York, New York, 1949, and in "Dye Lasers" by F. P. Schafer, Editor, Springer Publishers, Berlin, (1973). Others are described in "The Colour Index," Third Edition, Volume 4, The Society of Dyers and Colourists and The American Association of Textile Chemists and Colorists (1971).

The spectral distribution of the chemiluminescent emission from the composition of this invention is essentially the same as the fluorescence emission spectrum of the fluorescer compound employed.

Some specific examples of water-soluble fluorescer compounds of the class defined are as follows:

Rhodamine B (C.I. 45170)
Rhodamine 6G Perchlorate
Sulforhodamine B (C.I. 45100)
Sulforhodamine 101
9,10-Diphenylanthracene-2,6-disulfonic acid disodium salt
3,9-Perylenedisulfonic acid disodium salt
3,10-Perylenedisulfonic acid disodium salt 8-Hydroxy-1,3,6-pyrenetrisulfonic acid trisodium salt
Rhodamine 6G (C.I. 45160)
Disodium fluorescein (C.I. 45350:1)
Sulforhodamine G (C.I. 45220) and the like The preferred water-soluble fluorescer is the trisodium salt of 8-hydroxy-1,3,6-pyrenetrisulfonic acid.

The hydrogen peroxide compound employed in the composition and processes of this invention may be an aqueous solution of hydrogen peroxide per se, or a hydrogen peroxide-producing compound, such as sodium perborate, potassium perborate, sodium carbonate peroxyhydrate, histidine perhydrate, and the like.

It has been found that the molar concentrations (moles per liter of solution) of the major components of the novel compositions, described herein, may vary considerably. It is only necessary that the components be present in sufficient concentration to obtain chemiluminescence. The molar concentration of the oxamide normally is in the range of $10^{-3}$ to 5, preferably about $10^{-2}$ to 1.0. The molar concentration of the fluorescer compound used is from about $10^{-5}$ to $10^{-1}$, preferably $10^{-4}$ to $10^{-2}$. The molar concentration of the hydrogen peroxide compound used is from about $10^{-3}$ to 10.0, preferably $10^{-1}$ to 4.0. The optimum mole ratio of hydrogen peroxide compound to oxamide used ranges from about 0.5 to 10.0.

The ingredients of the chemiluminescent compositions of this invention are dept separated until chemiluminescence is desired, when they may be admixed in a single step or in a series of steps. The order of admixing of the ingredients is usually not critical. The hydrogen peroxide compound and fluorescer compound may be dissolved in water and the oxamide is added thereto to initiate chemiluminescence. The oxamide may be added as a solid or in a suitable diluent. Alternatively, the oxamide and the fluorescer compound may be dissolved in water and the hydrogen peroxide compound added thereto to initiate chemiluminescence. Preferably, the hydrogen peroxide compound in water is added to a solid mixture of oxamide and fluorescer to initiate chemiluminescence.

The intensity of the chemiluminescence is relatively independent of the pH of the reaction medium. Variation of the pH from about 3 to 8 has no discernible effect on the intensity of light emitted in the visible range.

Superior intensity of chemiluminescence is obtained when the final mixture producing the luminescence is maintained at a temperature from about $-10°$ to $50°$ C., preferably from about $15°$ to $40°$ C.

The invention is described in more detail by the following examples in which concentrations in moles per liter are indicated by the letter "M".

EXAMPLE 1

Preparation of N-(2-Morpholinoethyl)Trifluoromethanesulfonamide

Trifluoromethanesulfonic anhydride (40.46 grams; 0.143 mole) is added portionwise to a stirred solution of N-(2-aminoethyl)morpholine (37.34 grams; 0.286 mole) in methylene chloride (200 mls) at $0°$ C. under a nitrogen atmosphere. When the addition is completed, the mixture is stirred at room temperature for 3 hours. The white-solid precipitate is separated by filtration and the filtrate is evaporated to obtain 47.31 grams of crude product. Recrystallization of the crude product from cyclohexane gives the desired product (32.56 grams), m.p. $106°-108°$ C.

Calculated for $C_7H_{13}N_2O_3SF_3$: C, 32.06%; H, 4.96% N, 10.69%; S, 12.21%; F, 21.76%. Found: C, 32.08%; H, 4.87%; N, 10.54%; S, 12.02%; F, 21.50%.

In the manner described above, substituting N-(3-aminopropyl)morpholine (41.35 grams; 0.286 mole) for the N-(2-aminoethyl)morpholine and recrystallizing the crude product from methylcyclohexane, N-(3-morpholinopropyl)trifluoromethanesulfonamide is obtained, m.p. $95°-97°$ C.

Calculated for $C_8H_{15}N_2O_3SF_3$: C, 35.29%; H, 5.51%, N, 10.29%. Found: C, 35.33%; H, 5.52%; N, 10.05%.

EXAMPLE 2

Preparation of N,N'-Bis(2-Morpholinoethyl)-N,N'-Bis(Trifluoromethylsulfonyl)Oxamide Oxalyl chloride (11.10 grams; 0.076 mole) is added dropwise to a solution of N-(2-morpholinoethyl)trifluoromethanesulfonamide (37.72 grams; 0.152 mole) and triethylamine (15.39 grams; 0.153 mole) in dry tetrahydrofuran (400 mls) at $0°$ C. under a nitrogen atmosphere over a period of 90 minutes. After the addition is completed, the mixture is stirred at room temperature for 4 hours and then filtered. The filtrate is concentrated to remove tetrahydrofuran and obtain 34.36 grams of the crude product. Recrystallization of the crude product from petroleum ether gives the desired product, m.p. $62°-64°$ C.

Calculated for $C_{16}H_{24}N_4O_8S_2F_6$: C, 33.22%; H, 4.18%; N, 9.69%; S, 11.08%; F, 19.71%. Found: C, 33.49%; H, 4.29%; N, 9.74%; S, 10.86%; F, 19.45%.

In the manner described above, N,N'-bis(3-morpholinopropyl)-N,N'-bis(trifluoromethylsulfonyl)oxamide is prepared by substituting N-(3-morpholinopropyl)trifluoromethanesulfonamide (41.34 grams; 0.152 mole) for the N-(2-morpholinoethyl)trifluoromethanesulfonamide. Evaporation of the filtrate gives a yellow solid which on extraction with hot toluene and evaporation of the toluene extract gives the desired product, which melts at $112°-114°$ C. after recrystallization from a mixture of toluene and cyclohexane.

Calculated for $C_{18}H_{28}N_4S_2O_8F_6$: C, 35.64%; H, 4.62%; N, 9.24%. Found: C, 36.22%; H, 4.68%; N, 9.12%.

EXAMPLE 3

Preparation of 4,4'-{Oxalyl bis[[(trifluoromethyl)sulfonyl]imino]ethylene}Bis(4-methylmorpholinium trifluoromethanesulfonate)

Methyl trifluoromethanesulfonate (4.35 grams; 0.027 mole) is added portionwise to a solution of N,N'-bis-(2-morpholinoethyl)-N,N'-bis(trifluoromethylsulfonyl)oxamide (3.0 grams; 0.0052 mole) in methylene chloride (30 mls) at $0°$ C. under a nitrogen atmosphere. After the addition is completed, the mixture is stirred at room temperature for an additional 2 hours. The white-solid precipitate is then separated by filtration and washed several times with methylene chloride. After drying under vacuum, the product melts at $121°-125°$ C.

Calculated for $C_{20}H_{30}N_4O_{14}S_4F_{12}$: C, 26.49% H, 3.31%; N, 6.18%. Found: C, 26.28%; H, 3.16%; N, 6.13%.

Qualitative determination of chemiluminescence is carried out by adding an aqueous solution of a peroxide component comprising 1.5 M hydrogen peroxide and 0.0012 M sodium salicylate to a mixture of 0.1 gram of the above product and 0.01 gram of trisodium 8- hydroxy-1,3,6-pyrenetrisulfonate and examining the intensity of light emission in a dark room. The emission is rated moderate.

In the manner described above, substituting 0.01 gram of tetrasodium 1,3,6,8-pyrenetetrasulfonate for the trisodium 8-hydroxy-1,3,6-pyrenetrisulfonate, the emission of light is barely visible in a dark room.

EXAMPLE 4

Preparation of 4,4'-{Oxalyl bis[[(trifluoromethyl)sulfonyl]imino]ethylene}Bis(morpholinium chloride)

A solution of oxalyl chloride (11.10 grams; 0.076 mole) in dry tetrahydrofuran (50 mls) is added dropwise to a solution of N-(2-morpholinoethyl)trifluoromethanesulfonamide (37.72 grams; 0.152 mole) and triethylamine (15.39 grams; 0.153 mole) in dry tetrahydrofuran (400 mls) at 0° C. under a nitrogen atmosphere over a period of ninety minutes. The reaction mixture is then stirred at room temperature for an additional 4 hours and filtered to recover the white-solid precipitate (24.78 grams). The solid is then slurried in methylene chloride (150 mls) for 5 minutes and the remaining solid is recovered by filtration and dried to obtain 11.18 grams of the desired product, m.p. 142°–144° C.

Qualitative evaluation of the chemiluminescence of a system containing the above product, in the manner described in Example 3, results in a moderate emission of light.

EXAMPLE 5

Preparation of 4,4'-{Oxalyl bis[[(trifluoromethyl)sulfonyl]imino]ethylene}Bis(4-methylmorpholinium tetrafluoroborate)

Trimethyl oxonium tetrafluoroborate (1.1 grams; 0.0074 mole) is added rapidly to a solution of N,N'-bis-(2-morpholinoethyl)-N,N'-bis(trifluoromethylsulfonyl)oxamide (2.0 grams; 0.0035 mole) in methylene chloride (50 mls) at room temperature under a nitrogen atmosphere. The reaction mixture is stirred at room temperature for an additional 15 hours and the resulting white-solid precipitate is separated by filtration and washed successively with diethyl ether and ethyl acetate to obtain the desired product, m.p. 198°–204° C. (decomposition).

Qualitative evaluation of the chemiluminescence of a system containing the above product, in the manner described in Example 3, results in a moderate emission of light.

EXAMPLE 6

Preparation of 4,4'-{Oxalyl bis[[(trifluoromethyl)sulfonyl]imino]trimethylene}Bis(-morpholinium chloride)

Oxalyl chloride (11.10 grams; 0.076 mole) is added dropwise to a solution of N-(3-morpholinopropyl)trifluoromethanesulfonamide (41.34 grams; 0.152 mole) and triethylamine (15.39 grams; 0.153 mole) in dry tetrahydrofuran (400 mls) at 0° C. under a nitrogen atmosphere over a period of 90 minutes. After the addition is completed, the reaction mixture is stirred at room temperature for an additional 4 hours and then filtered. The filtrate is concentrated to remove the tetrahydrofuran and obtain a light-yellow solid. Extraction of the solid with hot toluene gives a toluene-insoluble product which is further washed with methylene chloride and dried under vacuum to obtain the desired product, m.p. 171°–173° C.

Calculated for $C_{18}H_{30}N_4S_2O_6Cl_2F_6$: C, 33.38%; H, 4.64%; N. 8.66%. Found: C, 33.07%; H, 4.74%; N, 8.40%.

Qualitative evaluation of the chemiluminescence of a system containing the above product, in the manner described in Example 3, results in a moderate emission of light.

EXAMPLE 7

Preparation of 4,4'-{Oxalyl bis[[(trifluoromethyl)sulfonyl]imino]trimethylene}-Bis(4-methylmorpholinium trifluoromethanesulfonate)

Methyl trifluoromethanesulfonate (2.18 grams; 0.013 mole) is added in portions to a solution of N,N'-bis-(3-morpholinopropyl)-N,N'-bis(trifluoromethylsulfonyl)oxamide (1.5 grams; 0.0026 mole) in methylene chloride (50 mls) at 0° C. under a nitrogen atmosphere. After the addition is completed, the mixture is stirred at room temperature for 2 hours. The white-solid precipitate is separated by filtration and washed with methylene chloride to obtain the desired product, m.p. 148°–150° C.

Calculated for $C_{22}H_{34}N_4O_{14}S_4F_{12}$: C, 28.27%; H, 3.64%; N, 6.00%. Found: C, 28.33%; H, 3.64%; N, 5.78%.

Qualitative evaluation of the chemiluminescence of a system containing the above product, in the manner described in Example 3, results in a moderate emission of light.

EXAMPLE 8

Preparation of 2,2'-{Oxalyl bis[[(trifluoromethyl)sulfonyl]imino]ethylene}Bis(1-methylpyridinium trifluoromethanesulfonate)

Methyl trifluoromethanesulfonate (0.72 gram; 0.004 mole) is added in portions to a solution of N,N'-bis[2-(2-pyridyl)ethyl]-N,N'-bis(trifluoromethylsulfonyl)oxamide (0.5 gram; 0.0009 mole) in methylene chloride (30 mls) at 0° C. under a nitrogen atmosphere. After the addition is completed, the reaction mixture is stirred at room temperature for 2 hours. The white solid is separated by filtration and washed with methylene chloride to obtain the desired product, m.p. 162°–165° C.

Calculated for $C_{22}H_{22}N_4O_{12}S_4F_{12}$: C, 29.66% H, 2.47%; N, 6.69%. Found: C, 29.89%; H, 2.30%; N, 6.48%.

Qualitative evaluation of the chemiluminescence of a system containing the above product, in the manner described in Example 3, results in a moderate to weak emission of light.

EXAMPLES 9–12

Quantitative Determination of Chemiluminescence

Aqueous hydrogen peroxide (2.8 mls; 1.5 M), containing sodium salicylate (0.0012 M), is added to a cuvette containing a mixture of trisodium 8-hydroxy-1,3,6-pyrenetrisulfonate (0.01 gram; $1.9 \times 10^{-5}$ mole), and an amount of the compound under test to provide the molar concentrations indicated in Table I.

The emission intensity is then measured at 535 nm by means of a spectroradiometer-luminometer similar to that described by Roberts and Hirt [Appl. Spectrosc., 21, 250 (1967)] modified with a Jarrell-Ash Model 82-410 grating monochromator and an RCA C31034 photomultiplier with a gallium arsenide photocathode operated at 1300 V with dry ice cooling. Raw data are recorded digitally on a Hewlett-Packard 5150A thermal printer. Spectral response is corrected by calibration against a standard tungsten lamp. Absolute light intensities are obtained by deriving calibration constants based on the accepted fluorescence quantum yield (0.55) for quinine sulfate, as reported by Melkuish [N.Z. Sci. Tech., B, 37, 142 (1955)], in 0.1 N $H_2SO_4$, and by ferrioxalate actinometry [Hatchard et al., Proc. R. Soc. London, Ser. A, 235, 518 (1956)] of the exciting light. Chemiluminescence quantum yields in einsteins per mole of compound under test are calculated by monitoring the intensity decay at a single wavelength and calculating the intensity at each time interval in einsteins per second from the chemiluminescence spectrum. Chemiluminescence spectra are then corrected for intensity decay. The total area under the decay curve is calculated by using a combination of a Simpson's rule integration and an exponential extrapolation to infinite time as described by Roberts and Hirt. Data are processed by a Digital Equipment Corp. PDP-1140 computer. The results obtained are shown in Table I.

TABLE I

| Example | Reactant | Reactant Concentration Mole/Liter | Percent Quantum Yield[a] | Light Capacity[b] |
|---|---|---|---|---|
| 9 | Product of Example 3 | 0.04 | 0.01 | 0.10 |
| 10 | Product of Example 5 | 0.06 | 0.008 | 0.15 |
| 11 | Product of Example 7 | 0.25 | 0.01 | 0.07 |
| 12 | Product of Example 8 | 0.02 | 0.002 | 0.011 |

[a]Percent Quantum Yield = einsteins per mole of reactant × $10^2$
[b]Light Capacity = lumen hours per liter of emitting solution

EXAMPLES 13-14

Aqueous hydrogen peroxide (2.8 mls; 1.75 M), containing sodium salicylate (1.2×10⁻³ M), is added to a cuvette containing amounts of the compound of Example 3 and the fluorescer under test to provide molar concentrations of $4.04 \times 10^{-2}$ M and $6.8 \times 10^{-3}$ M, respectively. The reaction mixture is mixed thoroughly and the emission intensity is measured at the emission peak of the fluorescer versus time. The results obtained are shown in Table II.

TABLE II

| Example | Fluorescer | Light Capacity | Time ¾ (mins) | Percent Quantum Yield | Photopic Factor[c] |
|---|---|---|---|---|---|
| 13 | HPTS[a] | 0.084 | 20 | 0.0074 | 0.694 |
| 14 | DSDPA[b] | 0.473 | 24 | 0.08 | 0.360 |

[a]trisodium 8-hydroxy-1,3,6-pyrenetrisulfonate
[b]disodium 9,10-diphenylanthracene-2,6-disulfonate
[c]Photopic Factor is the number which defines the ability of the human eye to see the color of the emitted light.

EXAMPLES 15-16

The procedure of Examples 13 and 14 is repeated using aqueous hydrogen peroxide (2.5 mls; 1.75 M) containing sodium salicylate (1.2×10⁻³ M), and amounts of bis[2,4-dichloro-6-[(2-dimethylaminoethyl)-methylsulfamoyl]phenyl]oxalate dihydrochloride and the fluorescer under test to provide molar concentrations of $6.8 \times 10^{-2}$ M and $6.8 \times 10^{-3}$ M, respectively. The reaction mixture is mixed thoroughly and the emission intensity is measured at the emission peak of the fluorescer versus time. The results obtained are shown in Table III.

TABLE III

| Example | Fluorescer | Light Capacity | Time ¾ (mins) | Percent Quantum Yield |
|---|---|---|---|---|
| 15 | HPTS | 0.0055 | 2.5 | 0.0003 |
| 16 | DSDPA | 0.002 | 2.0 | 0.0002 |

Comparison of the above results with the results in Table II shows that the compositions of Examples 13 and 14 are quantitatively much more superior in light intensity and efficiency than the compositions of Examples 15 and 16. These examples illustrate the superiority of the compositions containing the water-soluble oxamides of the present invention.

We claim:

1. A composition for generating chemiluminescent emission comprising an aqueous solution of a water-soluble organic fluorescer having spectral emission in the range from about 330 to about 1000 nanometers and a water-soluble amide of oxalic acid represented by the formula:

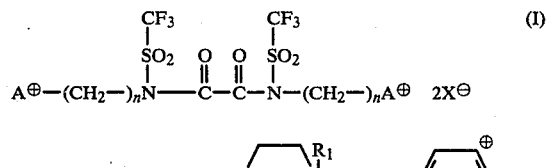

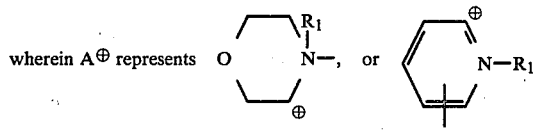

wherein $R_1$ represents hydrogen, or alkyl ($C_1$-$C_6$), n is an integer from 2 to 6, and $X^\ominus$ is an anion in proportions capable of producing chemiluminescence on reaction with hydrogen peroxide.

2. A composition, as defined in claim 1, wherein said amide is 4,4'-{Oxalyl bis[[(trifluoromethyl)sulfonyl]imino]ethylene}bis(4-methylmorpholinium trifluoromethanesulfonate).

3. A composition, as defined in claim 1, wherein said amine is 4,4'-{Oxalyl bis[[(trifluoromethyl)sulfonyl]imino]ethylene}bis(morpholinium chloride).

4. A composition, as defined in claim 1, wherein said amide is 4,4'-{Oxalyl bis[[(trifluoromethyl)sulfonyl]imino]ethylene}bis(4-methylmorpholinium tetrafluoroborate).

5. A composition, as defined in claim 1, wherein said amide is 4,4'-{Oxalyl bis[[(trifluoromethyl)sulfonyl]imino]trimethylene}bis(morpholinium chloride).

6. A composition, as defined in claim 1, wherein said amide is 4,4'-{Oxalyl bis[[(trifluoromethyl)sulfonyl]imino]trimethylene}bis(4-methylmorpholinium trifluoromethanesulfonate).

7. A composition, as defined in claim 1, wherein said amide is 2,2'-{Oxalyl bis[[(trifluoromethyl)sulfonyl]imino]ethylene}bis(1-methylpyridinium trifluoromethanesulfonate.

8. A composition defined by claim 1 wherein said water-soluble organic fluorescer is a tri-alkali-metal salt of 8-hydroxy-1,3,6-pyrenetrisulfonic acid.

9. A composition defined by claim 1 wherein said water-soluble organic fluorescer is a di-alkyl-metal salt of 9,10-diphenyl anthracene-2,6-disulfonic acid.

10. A process for generating chemiluminescence comprising adding an effective amount of a water-soluble amide of oxalic acid represented by the formula:

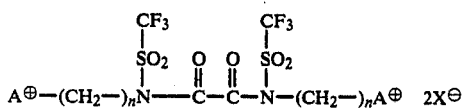

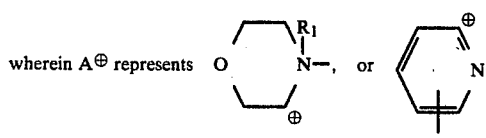

wherein $R_1$ represents hydrogen, or alkyl ($C_1$–$C_6$), n is an integer from 2 to 6, and $X^\ominus$ is an anion into an aqueous solution of hydrogen peroxide, or a source of hydrogen peroxide, and a solid water-soluble fluorescer compound having a spectral emission from about 330 to 1,000 nanometers.

11. A process for generating chemiluminescence comprising adding an effective amount of hydrogen peroxide, or a source of hydrogen peroxide, into an aqueous solution of a water-soluble amide of oxalic acid represented by the formula:

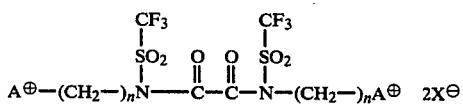

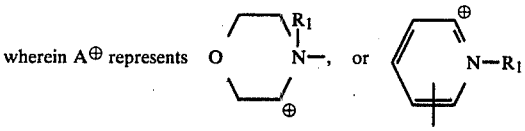

wherein $R_1$ represents hydrogen, or alkyl ($C_1$–$C_6$), n is an integer from 2 to 6, and $X^\ominus$ is an anion and a water-soluble fluorescer compound having spectral emission from about 330 to 1,000 nanometers.

12. A composition useful for generating chemiluminescence comprising a dry mixture of a water-soluble amide of oxalic acid represented by the formula:

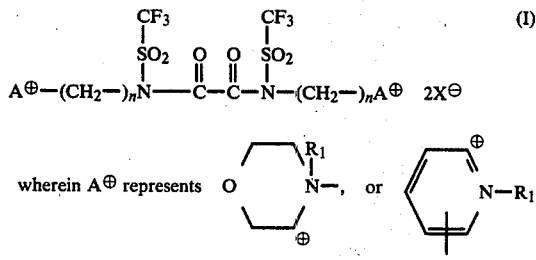

wherein $R_1$ represents hydrogen, or alkyl ($C_1$–$C_6$), n is an integer from 2 to 6, and $X^\ominus$ is an anion, a solid hydrogen peroxide source selected from the group consisting of sodium perborate, potassium perborate, sodium carbonate peroxyhydrate, and histidine perhydrate, and a solid water-soluble fluorescer in proportions capable of producing chemiluminescence when added to water.

13. The composition of claim 12 wherein the solid hydrogen peroxide source is sodium perborate.

14. A process for generating chemiluminescence comprising mixing the composition of claim 12 with water.

* * * * *